United States Patent
Kovach et al.

(10) Patent No.: US 7,008,413 B2
(45) Date of Patent: Mar. 7, 2006

(54) GENERIC MULTI-STEP THERAPEUTIC TREATMENT PROTOCOL

(75) Inventors: Peter J. Kovach, Fridley, MN (US); Craig R. Lang, Brooklyn Center, MN (US); David C. Ullestad, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 48 days.

(21) Appl. No.: 10/459,672

(22) Filed: Jun. 11, 2003

(65) Prior Publication Data

US 2003/0199854 A1  Oct. 23, 2003

Related U.S. Application Data

(62) Division of application No. 09/302,613, filed on Apr. 30, 1999, now Pat. No. 6,579,280.

(51) Int. Cl.
*A61K 9/22* (2006.01)
*A61N 1/08* (2006.01)

(52) U.S. Cl. ..................... 604/891.1; 607/59

(58) Field of Classification Search ............. 607/890.1, 607/891.1, 19–21, 30–31, 48, 131, 151, 93, 607/502, 45, 72, 59, 60
See application file for complete search history.

(56) References Cited

U.S. PATENT DOCUMENTS

| | | |
|---|---|---|
| 4,146,029 A | 3/1979 | Ellinwood |
| 4,373,527 A | 2/1983 | Fischell |
| 4,525,165 A | 6/1985 | Fischell |
| 4,559,037 A | 12/1985 | Franetzki et al. |
| 4,619,653 A | 10/1986 | Fischell |
| 4,692,147 A | 9/1987 | Duggan |
| 4,731,051 A | 3/1988 | Fischell |
| 5,370,672 A | 12/1994 | Fowler et al. |
| 5,569,186 A | 10/1996 | Lord et al. |
| 5,662,689 A | 9/1997 | Elsberry et al. |
| 5,713,922 A | 2/1998 | King |
| 5,735,814 A | 4/1998 | Elsberry et al. |
| 5,735,887 A | 4/1998 | Barreras, Sr. et al. |
| 5,782,798 A | 7/1998 | Rise |
| 5,814,014 A | 9/1998 | Elsberry et al. |
| 5,817,131 A | 10/1998 | Elsberry et al. |
| 5,840,069 A | 11/1998 | Robinson |
| 5,893,881 A | 4/1999 | Elsberry et al. |

(Continued)

FOREIGN PATENT DOCUMENTS

WO   WO09405355   3/1994

(Continued)

*Primary Examiner*—Jeffrey R. Jastrzab
(74) *Attorney, Agent, or Firm*—Banner & Witcoff, Ltd.

(57) ABSTRACT

A generic treatment protocol is disclosed for therapeutically treating a patient via an implantable treatment device. Treatment steps can be defined to start and end at absolute times, or can be programmed via telemetry to start a certain amount of time after termination of a previously executed treatment step. Treatment steps have a treatment rate or dose attribute and a duration attribute. Treatment steps may optionally enable patient-activated bolus overlays. Patient-activated rate or dosage adjustments can also optionally be enabled. Repeated-execution treatment-step groups are also provided. Such treatment-step groups can have start and end times, a group duration, and a group total dose, each defined in a manner similar to that for a treatment step. Treatment-step groups include a repetition count, which could be set to a value that causes the group to repeat forever. Single execution treatment steps can, accordingly, be programmed to execute before and/or after a repeated-execution treatment-step group.

24 Claims, 4 Drawing Sheets

U.S. PATENT DOCUMENTS

| | | |
|---|---|---|
| 6,024,539 A | 2/2000 | Blomquist |
| 6,036,459 A | 3/2000 | Robinson |
| 6,269,340 B1 | 7/2001 | Ford et al. |
| 6,635,048 B1 | 10/2003 | Ullestad et al. |

FOREIGN PATENT DOCUMENTS

| | | |
|---|---|---|
| WO | WO09709088 | 3/1997 |
| WO | WO9740874 | 11/1997 |

GENERIC MULTI-STEP THERAPEUTIC TREATMENT PROTOCOL

This application is a divisional of prior application Ser. No. 09/302,613, filed Apr. 30, 1999, now U.S. Pat. No. 6,579,280.

FIELD OF THE INVENTION

This invention relates to generic building blocks for specifying various modes of treating a patient via drug infusion or electrical nerve stimulation using a generic multi-step treatment protocol including single-execution treatment steps and repeated-execution treatment-step groups.

BACKGROUND OF THE INVENTION

Devices and techniques for treating neurological disorders by drug infusion and by electrical stimulation of a person's central nervous system are well known in the prior art. For instance, U.S. Pat. No. 5,713,922 to King, 5,782,798 to Rise, and U.S. Pat. No. 5,814,014 to Elsberry et al., each assigned to Medtronic, Inc. of Minneapolis, Minn., disclose such devices and techniques and are hereby incorporated by reference.

Such treatment devices and techniques often employ drug-infusion pumps and/or electrical pulse generators that are implanted within a patient's body. Accordingly, available memory for storing the parameters, such as treatment dose, duration, and timing, of various treatment protocols is severely limited. As a result, known implantable treatment devices are capable of storing a treatment protocol via telemetry that implements only a single treatment mode, such as single bolus, simple continuous, periodic bolus, or complex continuous treatment protocols. Single bolus refers to a non-recurring, finite treatment period. Simple continuous is a continuous treatment at a fixed treatment level. Periodic bolus refers to a single periodically recurring finite treatment period. Complex continuous refers to a plurality of treatment periods that periodically repeat themselves.

FIG. 2 depicts a prior art manner of specifying a complex continuous treatment protocol. The vertical axis represents the treatment rate. The horizontal axis represents elapsed time from the treatment protocol having been downlinked to the treatment device. In FIG. 2, the location of the vertical axis along the horizontal axis represents the time at which the treatment protocol was downloaded to the treatment device, as depicted at 100. For each example given in this document, the time at which the treatment prescription was downlinked to the treatment device will be assumed to be 3:00 PM, local time. In FIG. 2, a complex continuous treatment protocol is depicted in which a background rate of 20 microliters/hour is infused, as depicted at 102-1 through 102-8 (collectively 102). Note that, while the examples refer to infusion protocols, they are equally applicable to stimulation protocols. Background rate 102 is in effect when no treatment step is being performed.

The complex continuous treatment protocol depicted in FIG. 2 has the additional following attributes: the treatment cycle time is 24 hours; between 6:00 AM and 8:00 AM, 600 microliters is infused; between 11:00 AM and 1:00 PM, 200 microliters is infused; and between 9:00 PM and 11:00 PM, 500 microliters is infused.

In order to program such a treatment protocol using known prior art methods, treatment step 104-1, which corresponds to the 500 microliter treatment step from 9–11 PM, is programmed to start after a delay of 6 hours from the time the protocol is downlinked to the treatment device, namely, 3:00 PM. The treatment rate is determined by dividing the dose by the treatment-step duration, in this case 500 microliters divided by 2 hours, which is 250 microliters/hour. Accordingly, treatment step 104-1 would be programmed to include a delay from downlinking of 6 hours, during which the background treatment rate would be in effect, as depicted by 102-1. Treatment step 104-1 would also be programmed to provide treatment at 250 microliters/hour for 2 hours. Similarly, treatment step 106-1 would be programmed to include a delay from the completion of treatment step 104-1 of 7 hours, during which background treatment 102-2 would be in effect, and treatment at 300 microliters/hour for 2 hours. Treatment step 108-1 would be programmed to include a delay from the completion of treatment step 106-1 of 3 hours, during which background treatment 102-3 would be in effect, and treatment at 100 microliters/hour for 2 hours.

Following the completion of treatment step 108-1, background rate 102-4 would be in effect for the remaining 2 hours of the 24-hour treatment cycle.

Then, the 24-hour cycle would repeat itself in perpetuity or until a new treatment protocol is downlinked to the treatment device. Accordingly, background rates 102-5 through 102-8 of the second 24-hour treatment cycle shown in FIG. 2 correspond to background rates 102-1 through 102-4, respectively, of the first 24-hour treatment cycle shown in FIG. 2. Similarly, treatment steps 104-2, 106-2, and 108-2 of the second 24-hour treatment cycle shown in FIG. 2 correspond to treatment steps 104-1, 106-1, and 108-1, respectively, of the first 24-hour treatment cycle shown in FIG. 2.

Such known methods of specifying treatment protocols undesirably require that each time a change from one infusion mode, such as single bolus, simple continuous, periodic bolus, or complex continuous, to another infusion mode is desired, the new treatment protocol must be downlinked to the treatment device. In other words, known implantable treatment devices are incapable of storing multiple treatment-mode protocols. Patients and physician-programmers of such treatment devices are therefore severely inconvenienced by having to re-program such treatment devices each time an infusion mode change is made.

BRIEF SUMMARY OF THE INVENTION

It is therefore an object of this invention to overcome the shortcomings of the prior art by providing a generic treatment protocol for treating a patient via an implantable treatment device. The generic treatment protocol of this invention provides significantly improved versatility in implementing known treatment protocols, without the inconvenience of re-programming upon transitions between different treatment modes that is required when programming treatment protocols using prior art methods. In addition, the generic manner in which various treatment protocols can be specified using this invention also provides significant advantages for implementing newly created treatment protocols and for altering treatment protocols based on criteria such a patient travel between different time zones.

In one embodiment, the protocol includes a user-selectable number of one or more treatment steps, each having a corresponding duration, and one or more treatment-step groups, each having one or more treatment steps, a user-selectable treatment-step-group repetition count, and a user-selectable treatment-step-group duration. Additional aspects of the generic treatment protocol include: the capability of programming at least one of the treatment-steps to repeat forever; a series of single-execution treatment steps optionally executed initially upon programming the implantable treatment device; at least one of the treatment-step groups including: an absolute start time and an absolute end time, a start delay relative to completion of another treatment step, a user-selectable treatment rate, a user-selectable treatment dose, a patient-activated bolus, and/or a patient-activated rate adjustment.

In another embodiment of this invention, a therapeutic treatment device adapted to be implanted within a patient's body has a computer-readable medium that stores computer-executable instructions for providing a user-selectable number of one or more treatment steps for treating a patient using an implantable treatment device. Each of the treatment steps has a corresponding user-selectable treatment-step duration. In addition, the treatment-device computer-readable medium stores computer-executable instructions for providing one or more treatment-step groups. Each of the treatment-step groups includes: a user-selectable number of treatment steps; a user-selectable treatment-step-group repetition count; and a user-selectable treatment-step-group duration. The treatment-device computer-readable medium also contains further computer-executable instructions for performing steps analogous to the additional aspects of the generic treatment protocol set forth in the immediately preceding paragraph.

DETAILED DESCRIPTION OF THE INVENTION

Figure 1:
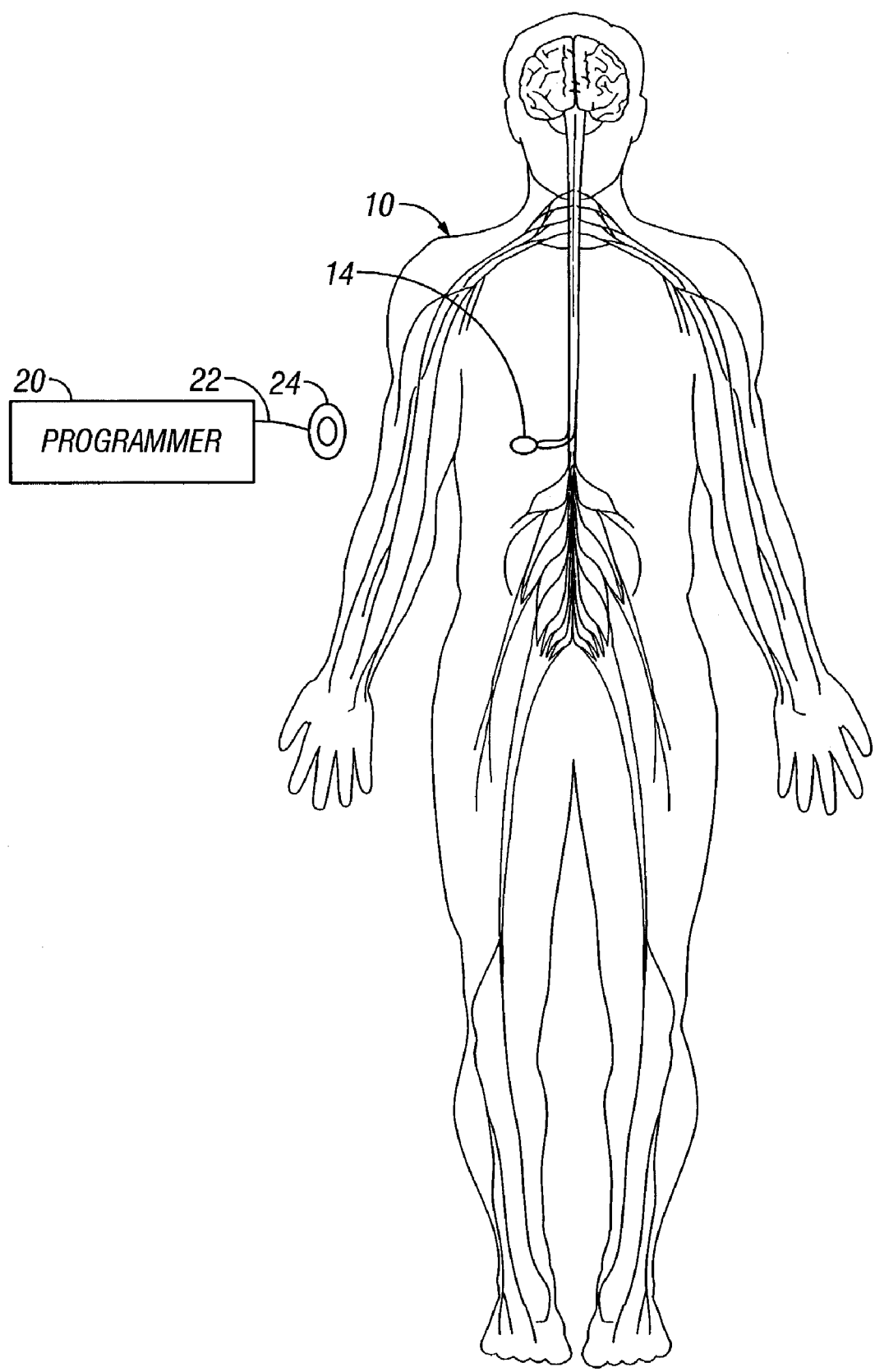
FIG. 1 is a schematic view of a patient with a treatment device implanted within the patient's body.

FIG. 1 is a schematic view of a patient 10 having treatment device 14 implanted within the patient's body. Implantable treatment device 14 is programmable through a telemetry link from programmer 20, which is coupled via a conductor 22 to a radio frequency antenna 24. Treatment device 14 could be, but is not limited to being, a pump for infusing medicaments into a patient's body or an electrical nerve stimulator for stimulating a patient's nervous system.

The fundamental building block for specifying various treatment protocols according to this invention is referred to as a treatment step. Treatment steps may be specified to start after a predetermined delay relative to downlinking of the treatment protocol to the implanted device or relative to completion of the preceding treatment step or any other suitable point in time. In the alternative, a treatment step may have a specified absolute start time and/or date. A treatment step according to this invention will include a treatment rate or dose and a treatment duration. A treatment step could also specify whether or not a patient-activated bolus may overlay the treatment step and whether, and if so, how much, of a patient-activated rate adjustment is allowed during the treatment step.

Treatment steps according to this invention are typically specified as executing one time. By grouping one or more treatment steps into a treatment-step group, the group of one or more treatment steps can be specified to repeat according to the treatment-step group specifications. Treatment-step groups according to this invention include a start time and/or date, which can be specified as either a delay or as an absolute time and/or date, as is the case for treatment steps. Treatment-step groups may include the number of treatment steps in the group. Treatment-step groups can include a background rate, which specifies the treatment rate when no treatment step is in effect. A repetition count is also included. The repetition count is capable of indicating that the group should repeat forever. Treatment-step groups also have a duration or period. A treatment-step group could have a maximum dosage associated with the group.

In addition to treatment steps and treatment step groups, boluses could also be defined separately to include a start delay or start time and/or date, a treatment rate or dose, a treatment duration, and whether the bolus is low-priority patient-activated, or high-priority physician-activated. High priority boluses could always take precedence over treatment steps, while patient-activated boluses could take precedence only over treatment steps that specifically allow themselves to be overlaid by low-priority boluses.

Figure 2:
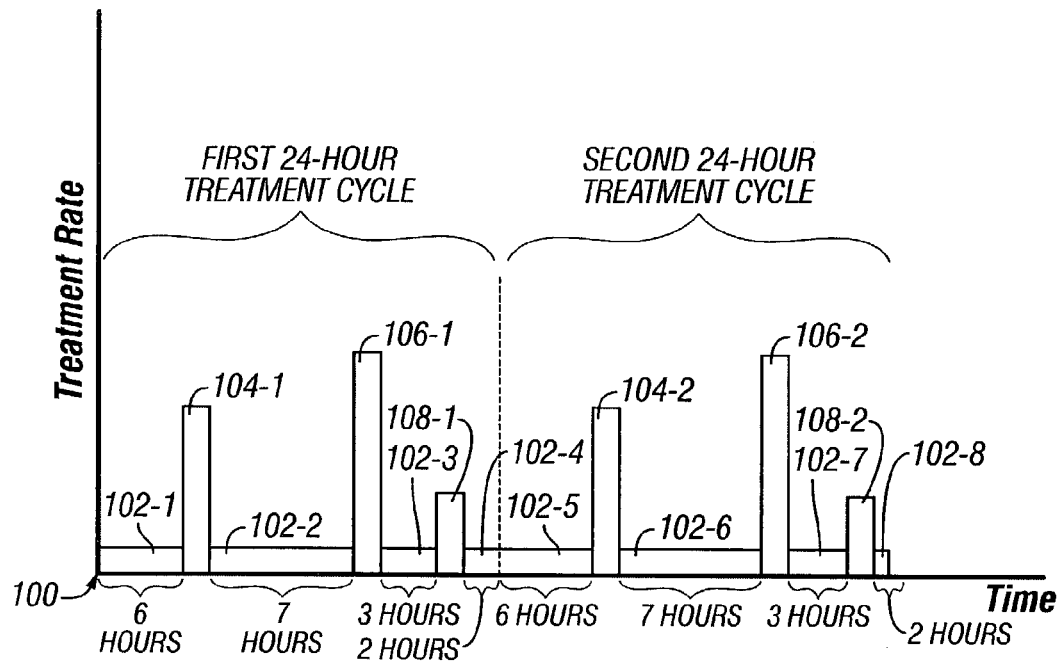
FIG. 2 depicts a complex continuous mode treatment protocol specified using prior art methods.
Figure 3:
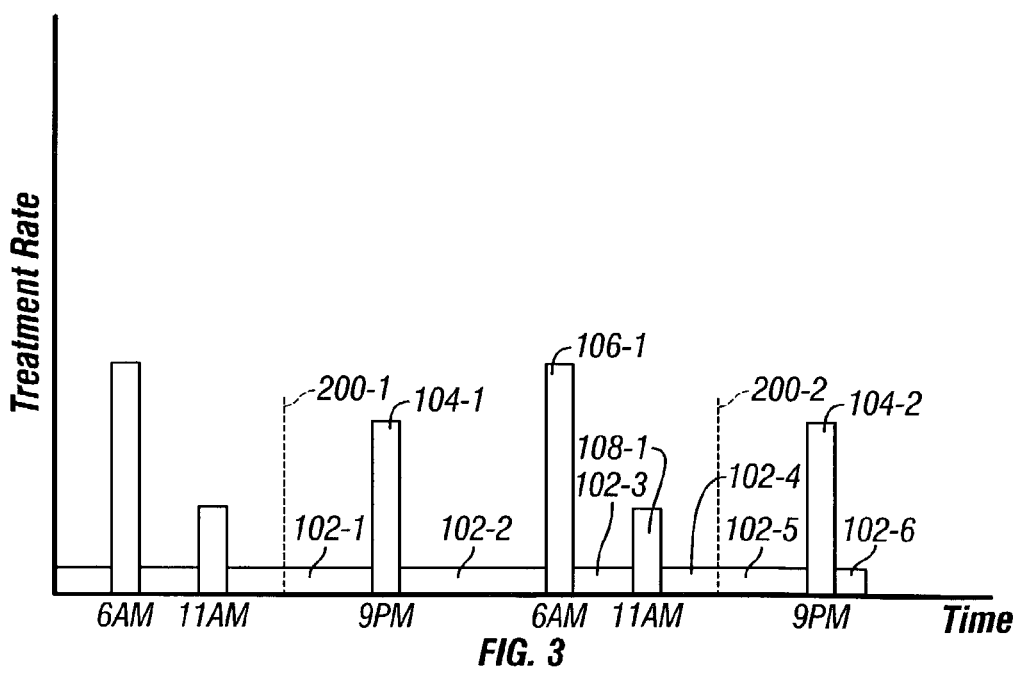
FIG. 3 depicts the same complex continuous mode treatment protocol as in FIG. 2, specified using the generic treatment protocol of this invention.

FIG. 3 depicts the complex continuous mode treatment protocol depicted in FIG. 2, but programmed or specified using the generic treatment protocol of this invention. The prescription parameters are the same, namely, the treatment cycle time is 24 hours; between 6:00 AM and 8:00 AM, 600 microliters is infused; between 11:00 AM and 1:00 PM, 200 microliters is infused; and between 9:00 PM and 11:00 PM, 500 microliters is infused. In addition, the complex continuous mode treatment protocol is downlinked to the treatment device at 3:00 PM, as depicted by dashed line 200-1. The treatment device automatically determines what treatment step or background rate should be executing at downlink time 200-1. Background rates 102-1 through 102-6 are the same as those depicted in FIG. 2 with the same reference numbers. However, the delays between treatment steps, such as treatment steps 104-1, 106-1, 108-1, and 104-2, may, but need not be specified. The generic treatment protocol of this invention provides backward compatibility so that physician programmers familiar with existing treatment protocol programming methods will be able to use this invention without learning anything new, if a physician programmer so desires. Nevertheless, treatment steps can be programmed using this invention by specifying treatment start time, a treatment end time, and a treatment rate or a treatment dose. Accordingly, instead of programming treatment step 104-1 as described above, namely, as a delay of 6 hours from the time the protocol is downlinked to the treatment device and as providing treatment at 250 microliters/hour for 2 hours, treatment step 104-1 could be programmed to provide 500 microliters between a treatment-step start time of 9:00 PM and a treatment-step end time of 11:00 PM. Treatment steps can also be specified as either allowing or not allowing a patient activated bolus and/or a patient-activated rate or dose adjustment. The physician-programmer may be provided with the option of disabling such patient-activated boluses and/or rate adjustments. A specified background rate can optionally be in effect for any period for which no treatment step is programmed.

In addition to programming specific treatment steps, treatment-step groups can be specified. For instance, the treatment steps 104-1, 106-1, and 108-1 could be defined as a treatment-step group including these three treatment steps. Such a treatment-step group could also include a repetition count specifying the number of times the treatment-step group should be executed. The treatment-step group could also be programmed to repeat forever. The duration of the treatment-step group is also programmable/user-selectable, which is advantageous for certain treatments having a treatment cycle time other than 24 hours, such as certain types of chemotherapy. The treatment-step group also may include a maximum incremental dosage for each iteration of a treatment-step group.

Figure 4:
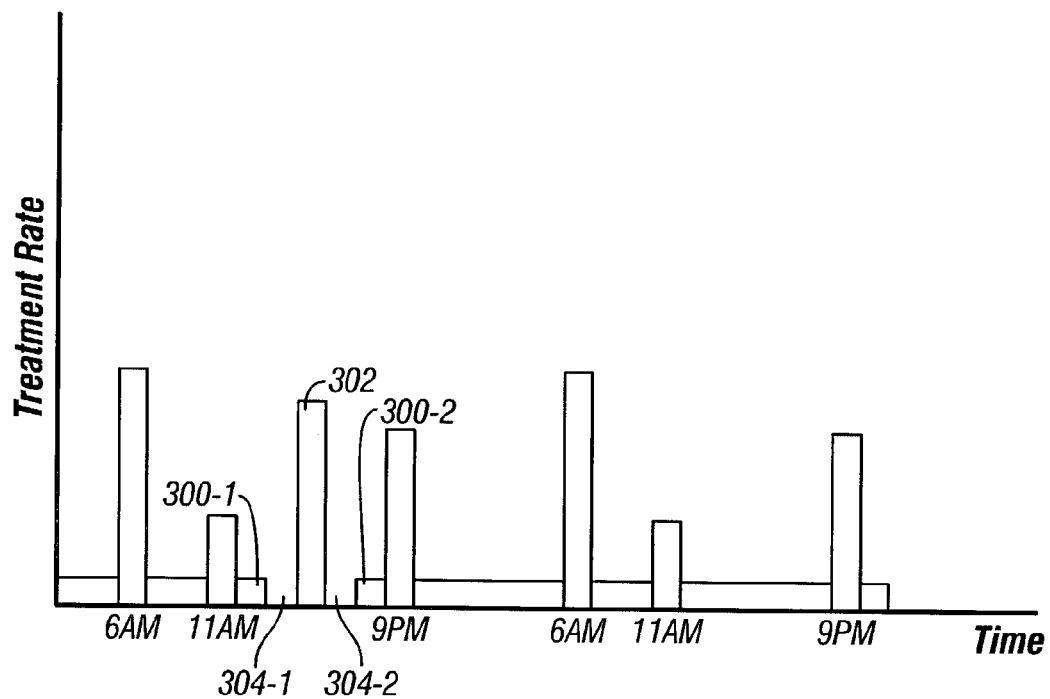
FIG. 4 depicts a complex continuous mode treatment protocol and a bolus.

FIG. 4 depicts an exemplary programmed treatment protocol including a bolus followed by a complex continuous mode treatment protocol according to the following parameters: background rate: 60 microliters/hour; group duration: 24 hours; 6–8 AM: 600 microliters; 11 AM–1 PM: 250 microliters; and 9–11 PM: 400 microliters. Bolus 302 of FIG. 4 is depicted as having been programmed according to the following parameters: 12–2 PM, 0 microliters; 2–4 PM, 500 microliters/hour; and 4–8 PM, 0 microliters/hour. The background rate of 60 microliters/hour is in effect as depicted at 300-1. The treatment device is programmed off, which overrides the background rate, before and after the bolus 302. The periods during which the treatment device is off are depicted as 304-1 and 304-2, respectively.

Figure 5:
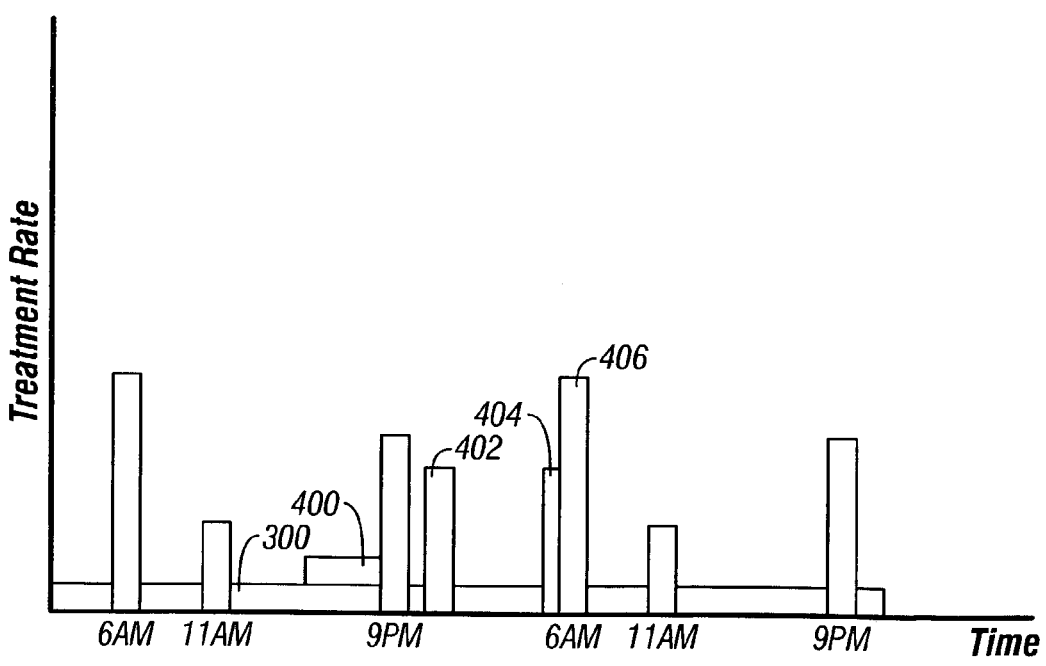
FIG. 5 depicts the same complex continuous mode treatment protocol as in FIG. 4, a patient-activated rate increase, and two patient-activated boluses.

FIG. 5 depicts a patient rate adjustment 400, a patient-activated bolus 402, and the interaction between a patient-activated bolus 404 that partially overlaps, and is locked-out by, treatment step 406, which has been programmed to disable patient-activated boluses. The complex continuous treatment mode prescription depicted in FIG. 5 has the same attributes as the complex continuous treatment prescription shown in FIG. 4, namely, background rate: 60 microliters/hour; group duration: 24 hours; 6–8 AM: 600 microliters; 11 AM–1 PM: 250 microliters; and 9–11 PM: 400 microliters. In addition, the 6–8 AM treatment step also specifies that patient boluses are disabled during that treatment step. Patient-activated rate increase 400 is depicted as having been programmed as a rate increase of 60 microliters per hour from 4–9 PM over background rate 300. Patient bolus 402 is depicted as having been programmed as 300 microliters per hour from 12–2 AM. Although a patient bolus is attempted from 5–7 AM at 300 microliters per hour, only the portion of the patient bolus from 5–6 AM will actually be administered because from 6–7 AM, patient boluses have been specifically disabled during programming of treatment step 406. Alternatively, a low-priority patient-activated bolus could be disabled in its entirety if any portion of the patient-activated bolus comes within a pre-determined time window either before or after a treatment step that disables patient-activated boluses. In addition to patient-activated low priority boluses, physician-programmer high priority boluses may also be specified. High priority boluses are always executed regardless of whether a particular treatment step has enabled patient-activated boluses. As used herein, the term user refers to a physician who programs the treatment device, as opposed to a patient within whom the treatment device is implanted.

Figure 6:
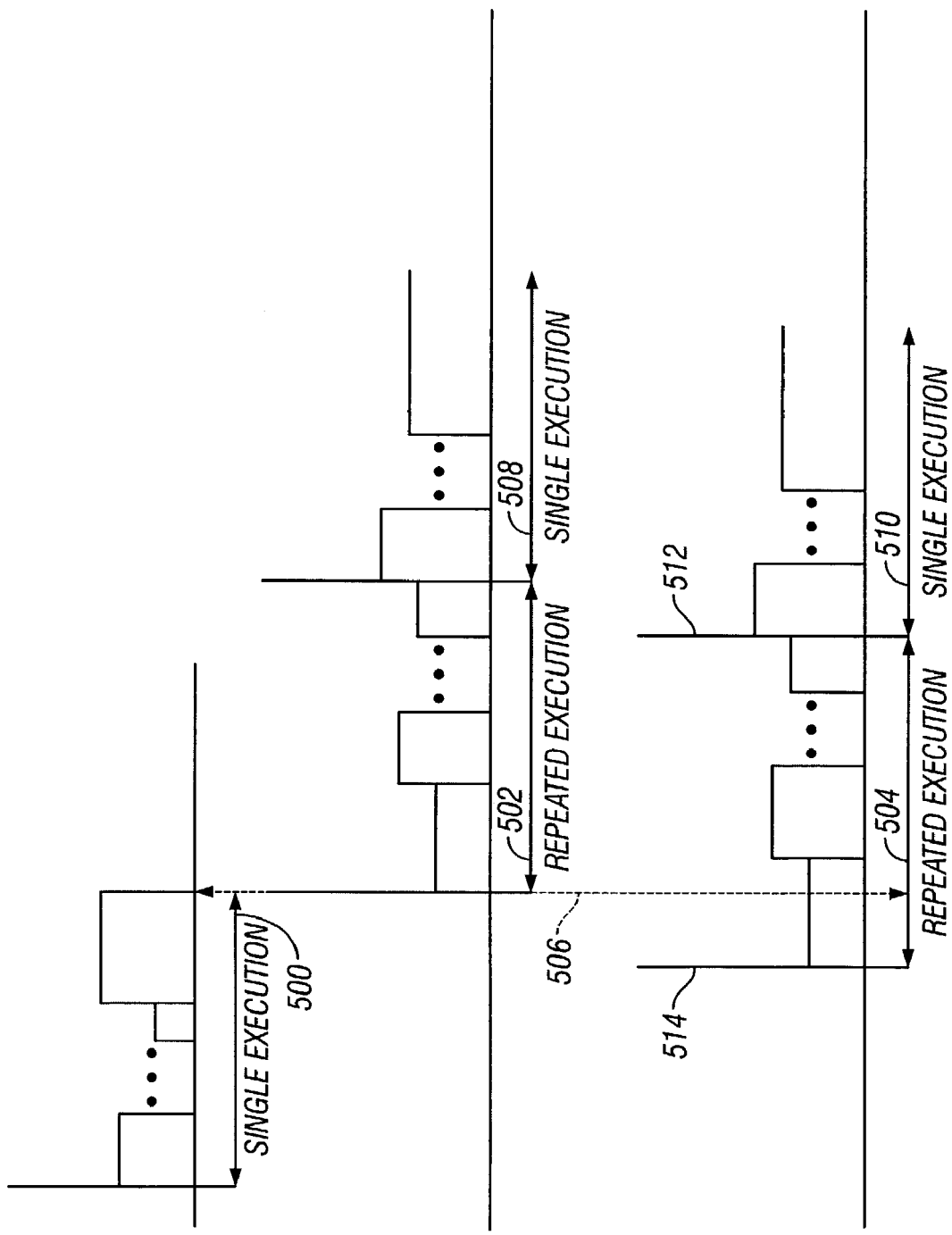
FIG. 6 depicts two different ways of transitioning from single-execution treatment steps to a repeated-execution treatment-step group.

FIG. 6 depicts a set of single execution treatment steps, spanned by double-headed arrow 500, that can optionally be executed before repeated execution of a treatment-step group, two of which are spanned by double-headed arrows 502 and 504. Double-headed and dashed arrow 506 represents the time at which the single execution treatment steps 500 terminate. Repeated-execution of treatment-step group 502 is depicted as starting upon termination of single execution treatment steps 500. This is a specific example of generically starting execution of a repeated-execution treatment-step group after a predetermined delay elapses relative to termination of single execution treatment steps 500. The predetermined delay between termination of single execution treatment steps 500 and repeated-execution treatment-step group 502 happens to be 0 seconds. As will be apparent, other suitable delays could also be used, as desired.

Repeated-execution treatment-step group 504 differs from repeated-execution treatment-step group 502 in the manner in which it begins executing upon termination of single-execution treatment steps 500. Repeated-execution treatment-step group 504 begins execution, not necessarily at the beginning of group 504, but at the point in time of group 504 that corresponds to termination of single execution steps 500. In other words, execution of repeated-execution treatment-step group 504 begins, or is picked-up, "in-progress" upon completion of single execution steps 500, as depicted at 506 in FIG. 6. Completion of each iteration of treatment-step group 504 is depicted at 512. Upon completion of the first iteration of repeated-execution treatment-step group 504, each following iteration of treatment-step group 504 starts at the beginning of group 504, which beginning is depicted at 514.

Following repeated execution treatment step groups 502 and 504 are single-execution steps 508 and 510, respectively. Single execution steps 508 and/or 510 may optionally be executed following a finite number of repetitions of repeated-execution treatment-step groups 502 and/or 504, respectively.

According to an aspect of this invention, the timing of a particular treatment protocol can be altered according to time zone changes. For instance, if a patient is planning to travel from the United States to Europe for a two-week vacation, the timing of treatment steps and/or treatment-step groups can be programmed to automatically adjust for the time zone change from the United States to Europe and to re-adjust the timing upon the expected return to the United States.

We claim:

1. A computer-readable medium containing computer-executable instructions that cause a human-implantable therapeutic treatment device to perform a specific therapeutic treatment protocol by performing steps comprising:

performing at least one treatment step that is defined, at least in part, by generic treatment parameters including a treatment rate or dose and a treatment duration, which have been downlinked to the treatment device;

performing at least one treatment-step group a number of times that is specified by a treatment-step-group repetition count that has been downlinked to the treatment device; and administering at least one activated bolus in accordance with downlinked generic treatment parameters including:

a start delay or start time, a treatment rate or dose, and a treatment duration.

2. The computer-readable medium of claim 1, wherein the at least one treatment step starts executing after a programmed delay relative to when the generic treatment protocol parameters are downlinked to the implantable device.

3. The computer-readable medium of claim 1, wherein the at least one treatment step is programmed to start executing after a predetermined amount of time elapses following completion of a preceding treatment step.

4. The computer-readable medium of claim 1, wherein the at least one treatment step starts executing at a programmed absolute start time.

5. The computer-readable medium of claim 1, comprising further computer-executable instructions for performing a patient-activated bolus while performing the at least one treatment step.

6. The computer-readable medium of claim 5, comprising further computer-executable instructions for disallowing an attempted patient-activated rate adjustment that would exceed a programmed maximum rate adjustment for the at least one treatment step.

7. The computer-readable medium of claim 1, wherein the at least one treatment-step group starts and ends in accordance with an absolute start time and an absolute end time, respectively.

8. The computer-readable medium of claim 1, wherein the at least one treatment-step group starts in accordance with a programmed delay relative to completion of an earlier executed treatment step.

9. The computer-readable medium of claim 1, wherein the at least one treatment step group includes providing treatment at a background rate when no treatment step is actively providing treatment.

10. The computer-readable medium of claim 1, wherein a maximum amount of treatment administered by the at least one treatment-step group is limited by a programmed maximum dosage.

11. The computer-readable medium of claim 1, wherein the treatment-step-group repetition count specifies that the at least one treatment-step group should repeat forever.

12. The computer-readable medium of claim 1, wherein the bolus includes a programmed priority that specifies that the bolus has a priority selected from the group consisting of:
    a low-priority patient-activated bolus that takes precedence over treatment steps that specifically allow themselves to be overlaid by low-priority boluses, and
    a high-priority physician-activated bolus that takes precedence over treatment steps.

13. A system for causing a human-implantable therapeutic treatment device to perform a specific therapeutic treatment protocol, the system comprising:
    means for performing at least one treatment step that is defined, at least in part, by generic treatment parameters including a treatment rate or dose and a treatment duration, which have been downlinked to the treatment device;
    means for performing at least one treatment-step group a number of times that is specified by a treatment-step-group repetition count that has been downlinked to the treatment device; and
    means for administering at least one activated bolus in accordance with downlinked generic treatment parameters including:
    a start delay or start time,
    a treatment rate or dose, and
    a treatment duration.

14. The system of claim 13, wherein the at least one treatment step starts executing after a programmed delay relative to when the generic treatment protocol parameters are downlinked to the implantable device.

15. The system of claim 13, wherein the at least one treatment step is programmed to start executing after a predetermined amount of time elapses following completion of a preceding treatment step.

16. The system of claim 13, wherein the at least one treatment step starts executing at a programmed absolute start time.

17. The system of claim 13, further comprising: means for performing a patient-activated bolus while performing the at least one treatment step.

18. The system of claim 13, further comprising: disallowing an attempted patient-activated rate adjustment that would exceed a programmed maximum rate adjustment for the at least one treatment step.

19. The system of claim 13, wherein the at least one treatment-step group starts and ends in accordance with an absolute start time and an absolute end time, respectively.

20. The system of claim 13, wherein the at least one treatment-step group starts in accordance with a programmed delay relative to completion of an earlier executed treatment step.

21. The system of claim 13, wherein the at least one treatment step group includes means for providing treatment at a background treatment while no treatment step is actively providing treatment.

22. The system of claim 13, wherein a maximum amount of treatment administered by the at least one treatment-step group is limited by a programmed maximum dosage.

23. The system of claim 13, wherein the treatment-step-group repetition count specifies that the at least one treatment-step group should repeat forever.

24. The system of claim 13, wherein the bolus includes a programmed priority that specifies that the bolus has a priority selected from the group consisting of:
    a low-priority patient-activated bolus that takes precedence over treatment steps that specifically allow themselves to be overlaid by low-priority boluses, and
    a high-priority physician-activated bolus that takes precedence over treatment steps.

* * * * *

UNITED STATES PATENT AND TRADEMARK OFFICE
CERTIFICATE OF CORRECTION

PATENT NO.        : 7,008,413 B2                                                                 Page 1 of 1
APPLICATION NO. : 10/459672
DATED             : March 7, 2006
INVENTOR(S)       : Kovach et al.

It is certified that error appears in the above-identified patent and that said Letters Patent is hereby corrected as shown below:

Col. 8. Line 25: "claim 13" should read --claim 17--

Signed and Sealed this

Fifth Day of December, 2006

JON W. DUDAS
*Director of the United States Patent and Trademark Office*